United States Patent

Shimizu et al.

4,056,310

Nov. 1, 1977

[54] METHOD AND DEVICE FOR OPHTHALMOSCOPY

[75] Inventors: Hiroyuki Shimizu, Utsunomiya; Kouji Inaba, Tokyo; Ken-Ichi Nakahashi, Hachiouji, all of Japan

[73] Assignee: Olympus Optical Co., Ltd., Tokyo, Japan

[21] Appl. No.: 658,053

[22] Filed: Feb. 13, 1976

[30] Foreign Application Priority Data

| Feb. 14, 1975 | Japan | 50-19729[U] |
| June 20, 1975 | Japan | 50-83571[U] |
| June 20, 1975 | Japan | 50-74358 |
| Sept. 12, 1975 | Japan | 50-110603 |
| Sept. 12, 1975 | Japan | 50-110604 |

[51] Int. Cl.² ............................ A61B 3/10; G02B 5/16
[52] U.S. Cl. ............................ 351/6; 350/96 B; 351/16
[58] Field of Search ................ 351/6, 7, 16; 350/96 B

[56] References Cited

U.S. PATENT DOCUMENTS

| 3,036,153 | 5/1962 | Day | 350/96 B X |
| 3,104,324 | 9/1963 | Rabinow | 350/96 B X |
| 3,475,082 | 10/1969 | Streitzel | 351/6 |
| 3,582,191 | 6/1971 | Cohen et al. | 351/6 X |
| 3,820,879 | 6/1974 | Frisen | 351/6 X |
| 3,944,341 | 3/1976 | Pomerantzeff | 351/6 X |
| 3,954,329 | 5/1976 | Pomerantzeff | 351/6 X |

*Primary Examiner*—Paul A. Sacher
*Attorney, Agent, or Firm*—Cushman, Darby & Cushman

[57] ABSTRACT

A method and device for ophthalmoscopy for observing fundus oculi by a binocular ophthalmoscope through a contact lens arranged in contact with an eyeball to be observed, said method and device for ophthalmoscopy enabling to observe the fundus by a multiplied erect image from a position distant from the examinee.

8 Claims, 17 Drawing Figures

METHOD AND DEVICE FOR OPHTHALMOSCOPY

BACKGROUND OF THE INVENTION a. Field of the Invention

The present invention relates to a method and device for ophthalmoscopy and, more particularly, to a method and device for observing and examining the fundus oculi of human eyes.

b. Description of the Prior Art

Out of known methods for observing the fundus oculi of human eyes, a positive lens is arranged at a position near the eyeball to be observed in one method and observation is made through said positive lens. In another known method, a contact lens is used so that the light will not be refracted by the surface of the cornea of the eyeball to be observed. Out of the above, the method to arrange the positive lens at a position near the eyeball to be observed and to observe through the positive lens has disadvantages that the observer should be skilled and experienced in this method and that the image obtained for observation is an inverted image. The disadvantage of this method that the image is inverted may be eliminated when the observer observes by letting his eyes closely approach said positive lens. In that case, however, the examinee will feel much oppressed because the observer closely approaches the examinee. Besides, the disadvantage that the observer should be skilled and experienced in this observing method cannot be still eliminated. Moreover, in this observing method, the fundus is illuminated through said positive lens. At that time, the illuminating light is reflected by the surface of the cornea and observation is disturbed by the reflected light.

The observing method to use the contact lens has various advantages. That is, in this method, observation is comparatively easy and, moreover, it is possible to observe an erect image. Besides, in this method, it is also possible to illuminate the fundus by means of optical fiber bundles arranged along the circumference of the contact lens. Therefore, comparatively favourable illumination can be attained. Moreover, when a large number of optical fiber bundles are arranged along the circumference of the contact lens, it is possible to illuminate a wide area of the fundus. The method to use the contact lens, however, has a disadvantage that the image to be observed cannot be magnified.

SUMMARY OF THE INVENTION

It is, therefore, a primary object of the present invention to provide a method and device for ophthalmoscopy in which a contact lens is arranged in contact with the eye to be observed and observation of the fundus oculi to be observed is made by a magnified erect image through said contact lens by means of a binocular ophthalmoscope comprising a binocular telescopic optical system.

Another object of the present invention is to provide a method and device for ophthalmoscopy in which optical fiber bundles for illumination are arranged along the circumference of the contact lens and observation of the fundus oculi to be observed is made through said contact lens by using the binocular ophthalmoscope by illuminating the fundus oculi through said optical fiber bundles.

Still another object of the present invention is to provide a method and device for ophthalmoscopy in which optical fiber bundles for illumination are arranged along the circumference of the contact lens so that illuminating light to be transmitted through them will exit in the direction of 10° through 20° in respect to the optical axis of the contact lens in order to eliminate the influence of reflection of illuminating light by the surface of the cornea.

Still another object of the present invention is to provide a method and device for ophthalmoscopy in which optical fiber bundles for illumination are arranged along the circumference of the contact lens so that the fundus oculi to be observed can be illuminated from one direction of the circumference of the contact lens by means of illuminating light selectively transmitted through at least one of said optical fiber bundles in order to eliminate the influence of reflection of illuminating light by the surface of cornea.

DETAILED DESCRIPTION OF THE PREFERRED EMBODIMENTS

The method and device for ophthalmoscopy according to the present invention are described in detail in the following referring to the accompanying drawings.

Figure 1:
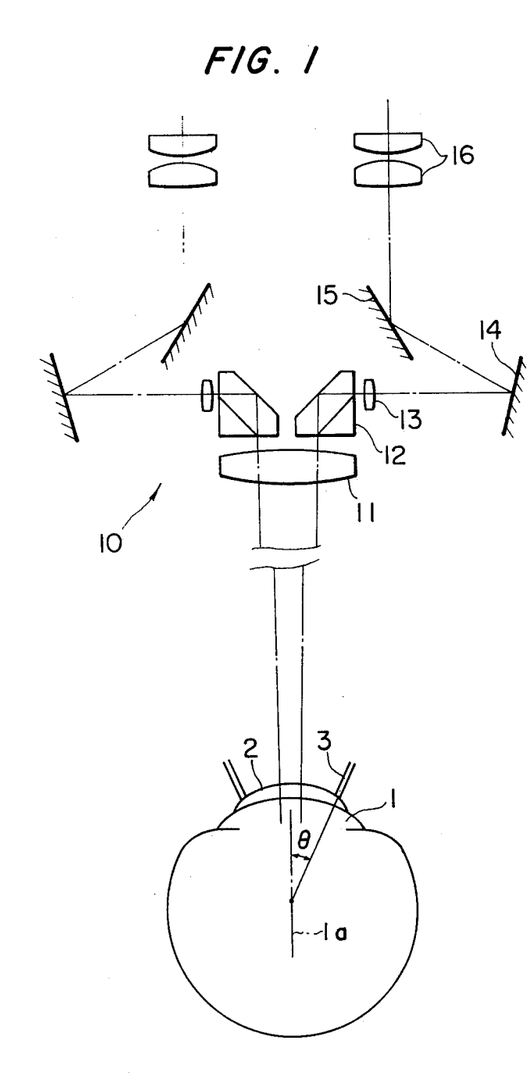
FIG. 1 shows a sectional view illustrating the optical system used in the method and device for ophthalmoscopy according to the present invention.

In FIG. 1, numeral 1 designates an eyeball to be observed. Numeral 2 designates a contact lens to which ends of a large number of optical fiber bundles 3 are fixed along the circumference thereof. Said contact lens 2 is similar to the known contact lens used in the known method in that said contact lens 2 is to be arranged so that one surface thereof closely contacts the surface of the cornea of the eyeball 1 to be observed and in that illuminating light for illuminating the fundus oculi is transmitted into the eyeball 1 through said optical fiber bundles 3 for the purpose of observation. Numeral 10 designates a binocular ophthalmoscope for observation of the fundus oculi to be arranged at a suitable distance from the contact lens 2. In said binocular ophthalmoscope, numeral 11 designates a positive lens, numeral 12 designates roof prisms, numeral 13 designates positive lenses, numerals 14 and 15 respectively designate reflecting mirrors, and numeral 16 designates eyepieces. Out of the above members 11 through 16, those other than the positive lens 11 are all arranged in pairs, i.e., for the right and left eyes of the observer. This optical system of the binocular ophthalmoscope is arranged so that objectives are formed by the positive lens 11 and respective positive lenses 13 and that Keplerian telescopes are formed by said objectives and eyepieces 16. As described in the above, the method for ophthalmoscopy according to the present invention is to use an optical system comprising a contact lens, which is arranged in contact with the cornea of the eye to be observed, and a binocular ophthalmoscope and to observe the image of the fundus oculi obtained through the contact lens by multiplying said image by means of the binocular ophthalmoscope.

As for illuminating light for illuminating the fundus oculi through optical fiber bundles 3, light from an ordinary light source may be all right. When, however, illuminating the fundus, observation is sometimes disturbed by the light reflected by the crystalline lens and the reflectivity at that time is higher for rays of shorter wavelengths. Therefore, for illuminating light, it is preferably to cut the rays of shorter wavelengths. Besides, the reflected light from the fundus, i.e., the light required for observation of the fundus, is of longer wavelengths, especially red light. When, therefore, the rays of shorter wavelengths are cut, it is possible to reduce the detrimental reflected light without causing any unfavourable influence on the light required for observation. Moreover, as the crystalline lens is formed by protein, auto-fluorescence may be caused. So, it is preferable to cut the ultraviolet rays, which will be absorved by the crystalline lens to cause auto-fluorescence and which are not necessary for observation. Due to the above-mentioned reason, a filter for cutting the rays of shorter wavelengths may be inserted between the light source and optical fiber bundle. In the case, wavelengths of rays to be cut by said filter are about 500 m$\mu$ and shorter.

In the above-mentioned method for ophthalmoscopy according to the present invention, observation is made by arranging the contact lens in contact with the cornea of the eye to be observed. Therefore, illuminating light transmitted through optical fiber bundles, which are arranged along the circumference of said contact lens, is not reflected by the cornea and it is possible to observe in favourable condition. Moreover, as said contact lens is used, refraction of light by the cornea is prevented and an erect image of the fundus is obtained for observation. Therefore, observation is very easy. Moreover, as the binocular ophthalmoscope is used for observation, the fundus can be observed by a stereoscopic image. Besides, as the binocular ophthalmoscope comprises a binocular Keplerian telescopic optical system, the field angle is large. Moreover, unlike the method for observing by arranging a positive lens in front of the eye to be observed, it is possible to observe the fundus from a position at a comparatively long distance from the examinee, the examinee will not feed oppressed.

In the method for ophthalmoscopy according to the present invention described in the above, reflection of light by various surfaces in the eye causes flare when the fundus of the eyeball 1 to be observed is illuminated by means of optical fiber bundles 3 arranged along the circumference of the contact lens 2, and it is somewhat inconvenient for observation. To prevent such flare, in the present invention, it is so arranged that the angle $\Theta$ between the advancing direction of the illuminating light coming out from the optical fiber bundles 3 and the optical axis of the contact lens 2 becomes a value within the range of 10° through 20°. Because of the above arrangement, reflected rays from surfaces of the homogeneous nucleus lentis, crystalline lengs, etc. do not come toward the observer. Therefore, it is possible to observe in good condition free from influence of illuminating light reflected by said various surfaces.

The angle of inclination of the optical fiber bundles 3, i.e., the angle $\theta$ between the advancing direction of the illuminating light coming out from the optical fiber bundles 3 and the optical axis of the contact lens 2, is selected as a value within the range of 10° through 20° dur to the reason described below.

Figure 2:
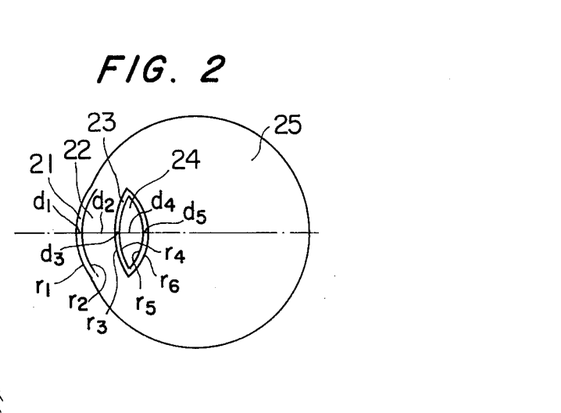
FIG. 2 shows a sectional view illustrating a model of eyeball.
Figure 3:
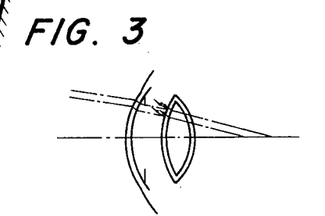
FIGS. 3 through 6 respectively show explanatory figures illustrating states of reflection of entrance rays by respective surfaces in the eyeball.
Figure 4:
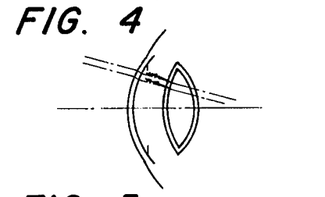
Figure 5:
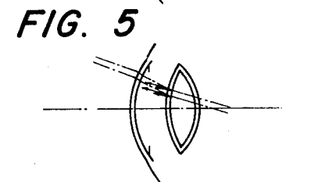
Figure 6:
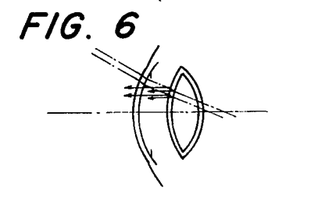

In FIG. 2 which shows construction of an eyeball, numeral 21 designates a cornea for which refractive index is 1.376, numeral 22 designates a camera bulbi anterior for which refractive index is 1.336, numeral 23 designates a homogeneous nucleus lentis for which refractive index is 1.385, numeral 24 designates a crystalline lens for which refractive index is 1.406, and numeral 25 designates a vitreous body for which refractive index is 1.336. Thicknesses of the above-mentioned members are respectively $d_1 = 0.5$ mm, $d_2 = 3.1$ mm, $d_3 = 0.546$ mm, $d_4 = 2.419$ mm and $d_5 = 0.635$ mm in the order from the cornea side toward the vitreous body side. Radii of curvature of respective surfaces in said eyeball are respectively $r_1 = 7.7$ mm, $r_2 = 6.8$ mm, $r_3 = 10.0$ mm, $r_4 = 7.911$ mm, $r_5 = -5.76$ mm and $r_6 = -6.0$ mm in the order starting from the outer surface of the cornea. The above-mentioned FIG. 2 shows average construction of humen eyeballs (based on Gullstrand's model). FIGS. 3 through 6 respectively show advancing directions of rays reflected by surfaces of the homogeneous nucleus lentis, christalline lens, etc. when the angle of inclination $\theta$, i.e., the angle between the optical axis 1a of said eyeball and advancing direction of entrance rays, is varied. In said FIGS. 3 through 6, said angle of inclination $\theta$ is 10° in FIG. 3, 15° in FIG. 4, 20° in FIG. 5 and 30° in FIG. 6. In case of FIG. 3 in which said angle of inclination $\theta$ is 10°, it is evident that the above-mentioned reflected rays from the homogeneous nucleus lentis, crystalline lens, etc. advance in the direction opposite to the optical axis 1a and, therefore, do not come toward the observer. In FIG. 4 in which said angle of inclination $\theta$ is 15°, rays reflected by surfaces of the crystalline lens etc. advance approximately toward the direction from which the entrance ray comes and, therefore, it is evident that said reflected rays do not come toward the observer. In FIG. 5 in which said angle of inclination $\theta$ is 20°, rays are reflected toward the side closer to the optical axis 1a in respect to the direction of incident rays. However, said reflected rays advance in the direction to part from the optical axis 1a and, therefore, do not come toward the observer. In FIG. 6 in which said angle of inclination $\theta$ is 30°, however, rays are reflected toward the direction which is approximately parallel with the optical axis 1a and advance toward the observer. Therefore, unfavourable influence is caused on observation. As described in the above, reflected rays from surfaces of the crystalline lens etc. cause unfavourable influence on observation when said angle of inclination θ exceeds 20°. Therefore, it is necessary to make the angle of inclination θ 20° or less. When the angle of inclination θ is small, it is possible to prevent unfavourable influence of rays reflected by surfaces of the crystalline lens etc. as explained in the 5 above. It is, however, not preferable to make the angle of inclination θ smaller than 10° due to the following reason. That is, due to the fact that the diameter of human eyeballs is approximately the same, the field angle available for observation becomes too small when the angle of inclination θ of optical fiber bundles, which are fixed along the circumference of the contact lens, becomes smaller than 10°. As a result of experiments, it has been confirmed that the most favourable angle of inclination θ is 15° ± 3°.

Figures 7, 8, 9:
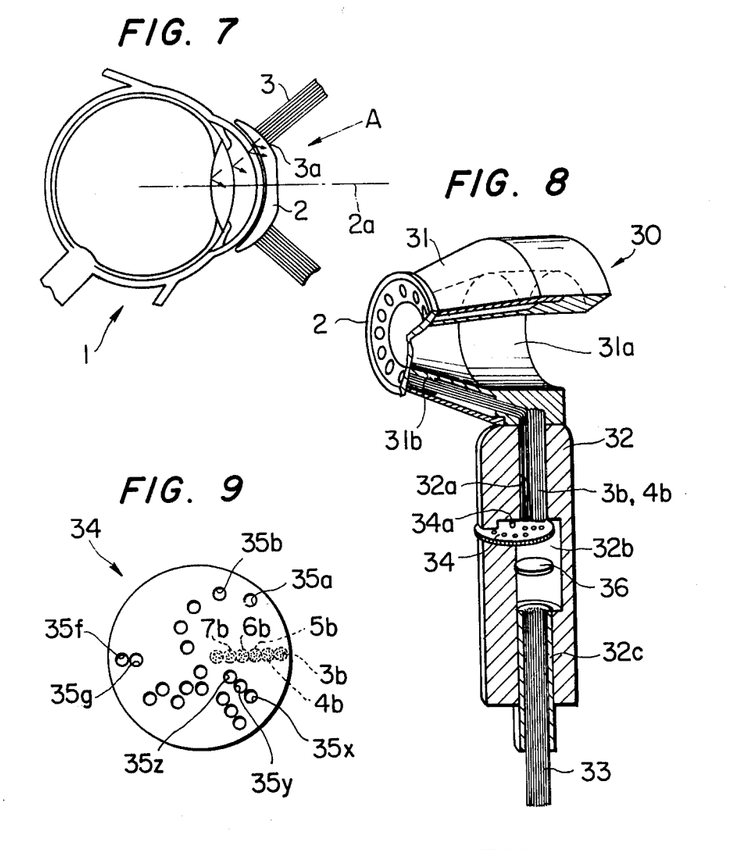
FIG. 7 shows an explanatory figure illustrating an example of the observing method according to the present invention.
FIG. 8 shows a perspective view of an example of the ophthalmoscope according to the present invention which is partially shown by sections.
FIGS. 9 and 10 respectively show plan views of examples of the selector shutter to be used in the ophthalmoscope shown in FIG. 8.

Now, another example of the observing method, which is free from detrimental influence of reflection of illuminating light by respective surfaces in the eyeball, is described below. Said observing method is to illuminate the fundus oculi by using a part of many optical fiber bundles arranged along the circumference of the contact lens and to observe in the direction approximately parallel to the direction of optical fiber bundles used for illumination at that time. In FIG. 7, the illuminating light is transmitted into the eyeball 1 through, for example, the optical fiber bundle 3 out of many optical fiber bundles 3, 4 . . . fixed along the circumference of the contact lens 2 and, at the same time, the fundus is observed in the direction shown by the allowhead A in FIG. 7. When, in this case, respective optical fibers are inclined at a lrge angle in respect to the optical axis 2a of the contact lens 2, the illuminating light from the optical fiber bundle 3 is reflected by respective surfaces in the eyeball and most of reflected rays advance in the direction parallel with the optical axis 2a of the contact lens 2 or toward the other side of the optical axis 2a, i.e., toward the right lower portion in FIG. 7. When, therefore, observed in the direction of the arrowhead A, reflected rays do not come toward the observer at all and it is possible to observe in favourable condition free from flare.

In this example of observing method, it is also possible to observe various portions of the fundus by selectively changing over the optical fiber bundle to be used for illumination among many optical fiber bundles 3, 4 . . . arranged along the circumference of the contact lens 1. That is, to observe a particular portion of the fundus, the entrance end of the optical fiber bundle may be selected so that the illuminating light is transmitted only to the exit end which corresponds to said particular portion of the fundus and observation is made in the direction approximately same as the direction in which the illuminating light goes out from the optical fiber bundle selected for illumination. Thus, it is possible to observe said particular portion of the fundus. When the optical fiber bundle to be used for illumination is selectively changed over and observation is made in the direction approximately same as the direction in which the illuminating light goes out from the exit end of the optical fiber bundle selected at that time, it is possible to observe or photograph a wide area of the fundus without being disturbed by flare or ghost image. When selecting the optical fiber bundle to be used for illumination, it is also possible to select a plural number of optical fiber bundles so that the illuminating light can be transmitted not only to one of exit ends of optical fiber bundles but to a plural number of continuously arranged exit ends out of exit ends arranged along the circumference of the contact lens. When so selected, it is possible to illuminate a wider portion of the fundus at a time.

An example of the concrete device utilizing the above-mentioned method is shown in FIG. 8. In FIG. 8, numeral 30 designates the device as a whole. Numeral 31 designates a holder carrying the contact lens 2 to be arranged in contact with the eyeball 1 to be observed. The holder 31 as a whole is formed substantially in a truncated conical shape with a hollow portion 31a at the center and said contact lens 2 is fixed to the smaller end of the holder 31. In the wall portion of the holder 31 around the hollow portion 31a, optical fiber bundles 3, 4 . . . are fixed by providing fixing holes 31b. Numeral 32 designates a handle to which said holder 31 is fixed at one end. The handle 32 has a hole 32a in which optical fiber bundles 3, 4 . . . are inserted. Besides, the handle 32 has a cavity 32b for housing a mechanism for changing over the optical fiber bundle to be selected for illumination and a hole 32c for fixing another optical fiber bundle 33 therein. Numeral 34 designates a selector shutter rotatably mounted in said cavity 32b of said handle 32 so that said selector shutter 34 rotates round a shaft 34a and arranged in such position that a circumferential portion thereof is exposed outside the handle 32 so that the selector shutter can be rotated from outside. FIG. 9 shows the shape of said selector shutter 34. As it is evident from FIG. 9, the selector shutter is formed as a disk and has a plural number of small holes 35a, 35b . . . which are formed by shifting little by little in radial and circumferential directions from the center toward the circumference of the disk. Numeral 36 designates a lens for condensing the illuminating light from the optical fiber bundle 33 onto the surface of the selector shutter 34.

Function of the above-mentioned device is as described below. At first, the contact lens 2 is applied to the eyeball 1 to be observed by holding the handle 32. Then, according to the required portion of the fundus to be observed, the selector shutter 34 is rotated so that the desired entrance end out of entrance ends 3b, 4b . . . of optical fiber bundles 3, 4 . . . is aligned with one of small holes 35a, 35b . . . of the selector shutter 34. Thus, the illuminating light transmitted from the light source by the optical fiber bundle 33 lights the surface of the selector shutter 34 by means of the lens 36 and is transmitted only by the optical fiber bundle 3, 4 or so aligned with the small hole 35a, 35b or so of the selector shutter 34 to illuminate the desired portion of the fundus.

Figure 10:
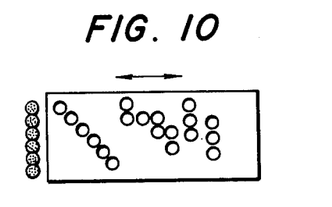

When it is desired to illuminate by using for example the optical fiber bundle 3, the small hole 35a of the selector shutter 34 is aligned with its entrance end 3b which is shown by dotted line in FIG. 9. As entrance ends 4b, 5b . . . of the other optical fiber bundles 4, 5 . . . are covered by the selector shutter 34, the illuminating light which lights the selector shutter 34 enters only to the optical fiber bundle 3 through the small hole 35a and is transmitted to the exit end of the optical fiber bundle 3. When small holes 35f and 35g are aligned with entrance ends 3b and 4b of optical fiber bundles 3 and 4, optical fiber bundles 3 and 4 only are used for illumination. When small holes 35x, 35y and 35z are respectively aligned with entrance ends 5b, 6b and 7b of optical fiber bundles 5, 6 and 7, optical fiber bundles 5, 6 and 7 are used for illumination. After selecting the optical fiber bundle or bundles as above, observation is made through the hollow portion 31a of the holder 31 in the direction which corresponds to the cirection A in FIG. 7 in respect to the selected optical fiber bundle or bundles. Thus, it is possible to observe or photograph the desired portion of the fundus without being disturbed by flare or ghost image because the rays reflected by the cornea, crystalline lens, etc. do not come toward the observer. When the selector shutter is rotated to change over the optical fiber bundle which aligns with its small hole and observation is made in the direction suitable for the optical fiber bundle selected for illumination, it is possible to observe the fundus by selecting its portion to be observed as desired. Besides, when the optical fiber bundle to be selected for illumination is changed over in turn as described in the above, it is possible to observe a wide area of the fundus. Moreover, when two or more optical fiber bundles are selected at a time, it is possible to illuminate a comparatively wide area of the fundus and it is possible to observe said area without being disturbed by flare or ghost image. The selector shutter shown in FIG. 9 is only an example. It is necessary to change the number, positions, etc. of small holes of the selector shuter according to the number of optical fiber bundles provided to the device. Besides, by suitably deciding the positions of small holes of the selector shutter, it is possible to select optical fiber bundles in various combinations. Moreover, the selector shutter is not limited only to the rotary type. It may be constructed in other types, for example, like the slide-type selector shutter shown in FIG. 10.

In the example shown in FIG. 8, the selector shutter, lens, etc. are provided in the handle. However, it is also possible to provide them in the light source unit for illuminating light instead of the handle. When, however, they are provided in the light source unit, it becomes impossible to change over the portion to be illuminated during observation by holding the handle by hand as in the case that they are provided in the handle as shown in FIG. 8. Therefore, the operation for changing over the optical fiber bundle to be selected becomes rather difficult. The light source may be also built in the handle 32 together with its power source.

Figure 11:
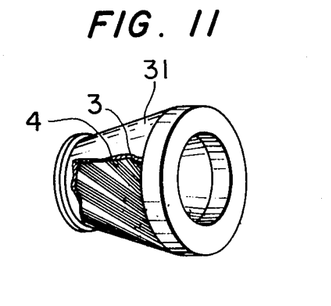
FIG. 11 shows a partially broken perspective view illustrating an example of arrangement of optical fiber bundles in the ophthalmoscope shown in FIG. 8.

In the example shown in FIG. 8, respective optical fiber bundles are fixed to the holder 31 so that productions of center lines of optical fiber bundle portions near their exit ends intersect with each other on the optical axis of the contact lens. However, it is also possible to mount said optical fiber bundles to the holder by arranging them helically, for example, as illustrated in FIG. 11. In this case, portions of respective optical fiber bundles near their exit ends are arranged in such planes which do not include the optical axis of the contact lens but are inclined toward pre-determined direction by a pre-determined angle. Therefore, productions of center lines of those portions of respective optical fiber bundles do not intersect with the optical axis of the contact lens. In case of this example shown in FIG. 11, it is more effective for eliminating the influence of flare and ghost image.

Figure 12:
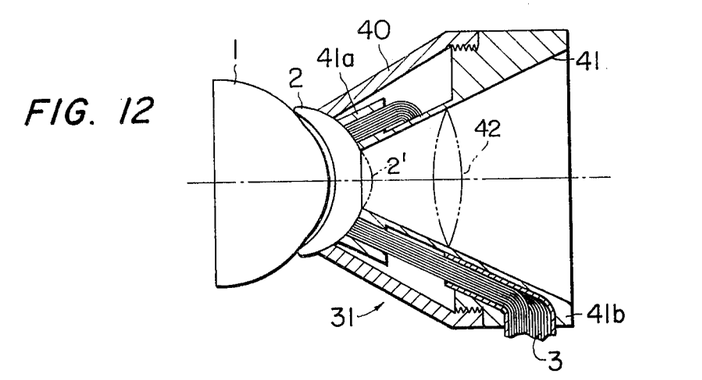
FIGS. 12 and 13 respectively show sectional views illustrating construction of a contact lens holder and optical fiber bundle holder of said ophthalmoscope.
Figure 13:
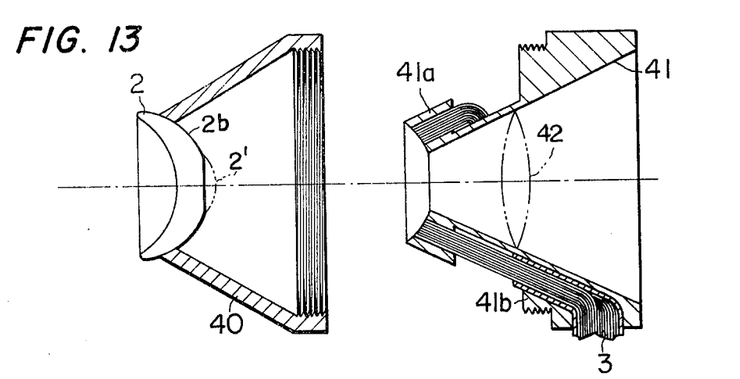

Out of respective members constituting the device 30 shown in FIG. 8, the holder 31 may be arranged by a contact lens holder 40 and optical fiber bundle holder 41 as shown by sectional views in FIG. 12 and FIG. 13 so that the holder 40 and holder 41 can be separated from each other, because it is then more convenient for sterilization and disinfection. For the holder 31 shown in FIG. 12 and FIG. 13, the contact lens holder 40 is formed substantially as a hollow truncated cone and the contact lens 2 is mounted to its smaller end by a suitable means, for example, by fixing the circumference of the contact lens by a binding agent. The optical fiber bundle holder 41 is also formed substantially as a hollow truncated cone and optical fiber bundles 3, 4 . . . are mounted to its outer surface. At one end portion 41a of the holder 41, holes are provided to insert and fix the exit end portions of optical fiber bundles 3, 4 . . . and, at the other end portion 41b, holes for passing optical fiber bundles 3, 4 . . . are provided. Besides, the end surface of the end portion 41a is formed as a curved surface which can be suitably fitted to the outer surface 2b (the surface opposite to the surface to contact the eyeball) of the contact lens 2. The contact lens holder 40 and optical fiber bundle holder 41 are arranged so that they can be separated from each other as shown in FIG. 13.

When it is so arranged that the contact lens holder 40 can be separated from the optical fiber bundle holder 41 as described in the above, it is possible to separate them from each other, as shown in FIG. 13, after completion of observation and to sterilize and disinfect the contact lens holder 40 only. That is, the optical fiber bundle holder 41 is inserted into the hollow portion of the contact lens holder 40 of hollow truncated-cone shape together with optical fiber bundles 3, 4 . . . arranged around the optical fiber bundle holder 41 and, therefore, it is not contaminated by the eye of the examinee at the time of observation. So, it is not necessary to disinfect the optical fiber bundle holder 41 and optical fiber bundles.

In the method for oph thalmoscopy described so far, the image to be observed is not multiplied and, therefore, it is somewhat inconvenient for observation. To eliminate this disadvantage, it is also possible to arrange so that the surface 2b of the contact lens 2 has positive refractive power as shown in a chain line 2' in FIG. 12 and FIG. 13 or to arrange a positive lens 42 as shown also by a chain line in order to multiply the image to be observed.

Figure 14:
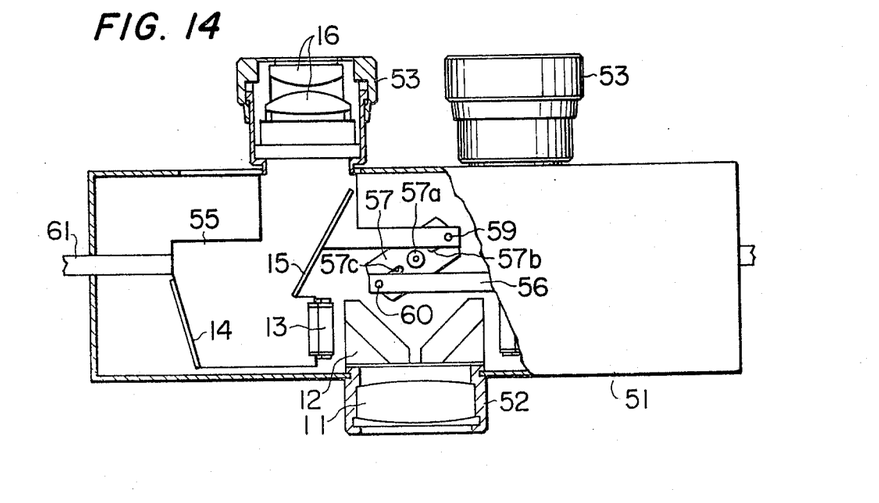
FIG. 14 shows a partially broken plan view of a head-band scope according to the present invention.
Figure 15:
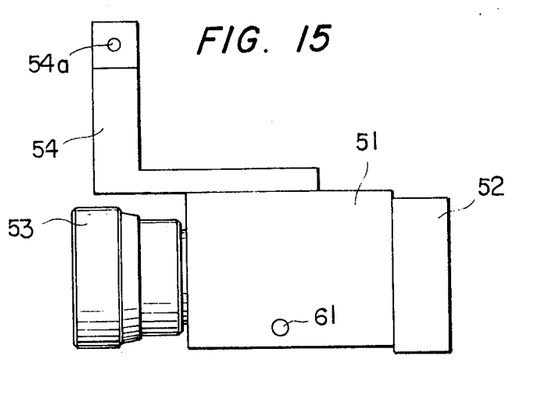
FIG. 15 shows a side view of said head-band scope.

When examining the fundus oculi by the method for ophthalmoscopy according to the present invention, it becomes necessary to record or sketch the content of observation immediately. Therefore, it is preferably to keep the observer's hands as far as possible free. To attain this object, in the present invention, the binocular ophthalmoscope comprising a binocular telescopic optical system and designated by numeral 10 in FIG. 1 is arranged as a head-band scope as shown in FIG. 14 and FIG. 15, i.e., it is so arranged that said binocular ophthalmoscope is supported on a head band. In FIG. 14 and FIG. 15, numerals 11 through 16 respectively designate optical elements such as lenses, reflecting mirrors, etc. which are substantially same as those shown in FIG. 1. Numeral 51 designates a box-type head-band scope body which houses the above-mentioned optical elements and to which a lens mount 52 and eyepiece mounts 53 are attached. Numeral 54 designates a fixture which is fixed to the body 51 and is provided for the purpose of mounting the head-band scope to a head band by utilizing a mounting hole 54a. Numeral 55 designates a first base plate to which the positive lens 13 and reflecting mirrors 14 and 15 on the left side in FIG. 14 are fixed. The first base plate is arranged so that it can be moved rightward and leftward as seen in FIG. 14. by a small amount along a suitable guide. Numeral 56 designates a second base plate to which the positive lens 13 and reflecting mirrors 14 and 15 on the right side in FIG. 14 are fixed and which is arranged to be movable to the right and left in the same way as the first base plate 55. To these base plates, eyepiece mounts 53 are connected respectively so that eyepiece mounts 53 can be respectively moved together with the corresponding base plates. Numeral 57 designates a connecting member which connects said first and second base plates 55 and 56 and is mounted to the body 51 so that the connecting member 57 can be rotated round a shaft 57a. The connecting member 57 has slots 57b and 57c. Numerals 59 and 60 respectively designate pins provided respectively to base plates 55 and 56 and inserted to said slots 57b and 57c in order to connect base plates 55 and 56 to each other. When, therefore, one of said base plates is moved, the other base plate also moves by the same amount toward the opposite direction. Consequently, eyepiece mounts movable integrally with said base plates are also moved and, lenses 13, reflecting mirrors 14 and 15 and eyepieces 16 on the right and left also move integrally but in opposite directions so that inter-ocular adjustment is made. Numeral 61 designates adjusting shafts respectively fixed to said base plates for the purpose of making interocular adjustment.

Figure 16:
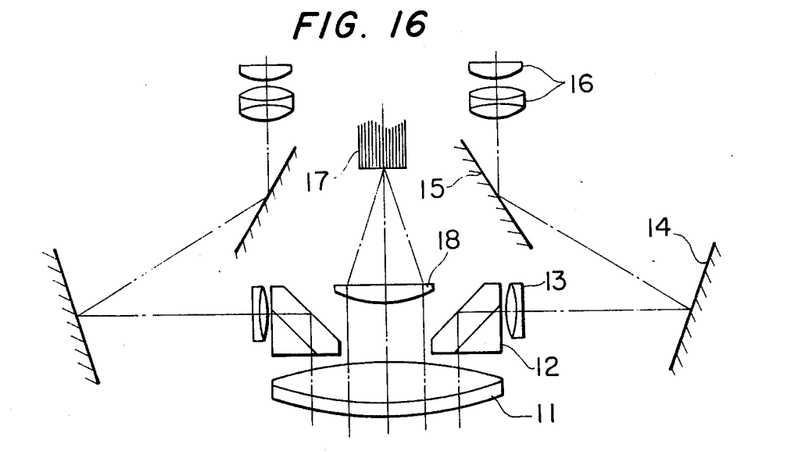
FIG. 16 and FIG. 17 respectively show sectional views illustrating alternative examples of the optical system of the binocular ophthalmoscope according to the present invention.

Effects of the head-band scope described in the above are as explained in the following. As shown in FIG. 1, the contact lens 2 is arranged in contact with the eyeball 1 to be observed and the fundus is illuminated by optical fiber bundles 3 arranged along the circumference of the contact lens 2. On the other hand, the observer fixes the head-band scope on his head and observes the fundus through eyepieces. Thus, it is possible to observe the fundus by a multiplied erect image. Moreover, as observation is made by both eyes, it is possible to observe the fundus by a stereoscopic image. As the head-band scope is fixed on the observer's head, it is not necessary to carry it by hand and the observer's hands are free to sketch the observed image or to perform other works. Moreover, the head-band scope can be used not only in combination with the contact lens but also in the known observing method in which a positive lens is arranged near the eyeball to be observed and the fundus is observed through said positive lens. Moreover, as the observer's both hands are completely free, it is possible to use this head-band scope in the same way as an operation microscope at the time of surgical operations. That is, by using this head-band scope, it is possible to perform operation on the fundus and other surgical operations by observing a multiplied image. When using said head-band scope for such operations, it is preferable to use a head-band scope comprising an optical system as shown in FIG. 16. In the optical system shown in FIG. 16, an exit end of an optical fiber bundle 17 and lens 18 are further provided between the right and left optical elements constituting the above-mentioned head-band scope. At the time of operation by using the head-band scope comprising the optical system shown in FIG. 16, the illuminating light transmitted through the optical fiber bundle 17 illuminates the portion to be operated on through the lens 18 and positive lens 11 and operation can be carried out by observing through the binocular optical system. When the head-band scope comprising the optical system shown in FIG. 16 is utilized in the known method for observing the fundus by using a positive lens, it is possible to observe the fundus by illuminating it by means of illuminating light from the optical fiber bundle 17 through the positive lens which is arranged near the eyeball to be observed.

Figure 17:
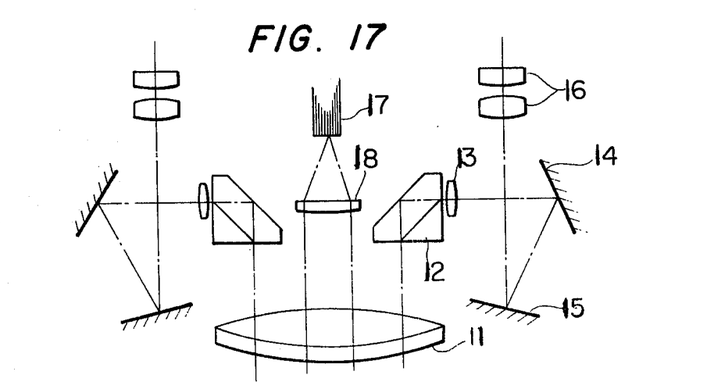

Now, another example of optical system is shown in FIG. 17. This optical system is basically same as the optical system shown in FIG. 1, FIG. 14 and FIG. 16 but is arranged compactly by changing the arrangement of reflecting mirrors.

When, in the above-mentioned optical system shown in FIGS. 14, 16 and 17, it is so arranged that rays passed through the positive lens 11 become parallel rays, the focusing position of the optical system does not change when inter-ocular adjustment is made by moving the positive lenses 13, reflecting mirrors 14 and 15 and eyepieces 16 integrally. When this head-band scope is used for operation on the fundus by arranging the contact lens in contact with the eyeball to be operated on, it is necessary to adopt some fixing means in order to prevent the contact lens from getting out of position during operation because of motion of the patient. As one of such means, it is possible to form small holes along the circumference of the contact lens and to sew the contact lens to the eyelid by utilizing those small holes. Thus, it is possible to operate on the fundus by using the head-band scope according to the present invention.

When using the above-mentioned head-band scope, the operator's hands are kept completely free during observation and, therefore, it is very convenient as it is possible to record or sketch the content of observation or to carry out other works at the same time as observation. Moreover, by utilizing the above-mentioned advantage, this head-band scope can be used for various applications, for example, as an operation microscope. Besides, as this head-band scope is of the binocular type, it is possible to observe the object by a multiplied stereoscopic image. As the image obtained is an erect image, it is more convenient for observation and operation. In addition, at the time of examination of the fundus etc., the observer can observe from a position comparatively distant from the patient. Therefore, it is possible to prevent the patient from feeling oppressed. Thus, this head-band scope has various advantages.

Moreover, when it is so arranged that the end face of the optical fiber bundle 17 comes to the focal plane of the lens 18, rays of illuminating light passed through the lens 18 becomes parallel rays. Therefore, said rays are condensed by the positive lens 11 onto the object to be observed such as the fundus, and it is possible to attain favourable illumination. Furthermore, even when the positive lens 11 is exchanged in order to change magnification, favourable illumination can be attained in the same way.

We claim:

1. A method for ophthalmoscopy comprising the steps of arranging a contact lens in contact with an eyeball to be observed in order to observe the eyeball by eliminating refraction of light by the surface of the cornea of the eyeball, illuminating the fundus of the eyeball by transmitting illuminating light through a plurality of optical fiber bundles having exit ends arranged along the circumference of the contact lens and entrance ends arranged opposite to a light source, and observing a magnified erect image by means of a head-band scope comprising a binocular telescopic optical system arranged opposite to and distant from the contact lens.

2. A method for ophthalmoscopy according to claim 1, in which rays of illuminating light from said optical fiber bundles advance in a direction within the range of 10° through 20° in respect to the optical axis of said contact lens.

3. A method for ophthalmoscopy according to claim 1, in which the fundus of said eyeball is illuminated by illuminating light selectively transmitted by at least one of said optical fiber bundles and in which said fundus is observed from a position corresponding to the exit end of the selected optical fiber bundle.

4. A device for ophthalmoscopy comprising a contact lens, a plurality of optical fiber bundles having exit ends fixed along the circumference of said contact lens by inclining said exit ends by 10° through 20° with respect to the optical axis of the contact lens, a tubular holder carrying said contact lens at one end thereof and carrying said optical fiber bundles arranged in substantially longitudinal direction of the holder, and a selector shutter arranged adjacent to entrance ends of said optical fiber bundles for the purpose of selectively transmitting the illuminating light by means of said optical fiber bundles, said device for ophthalmoscopy being arranged to selectively transmit illuminating light by means of at least one of said optical fiber bundles by operating said selector shutter for the purpose of illuminating the fundus of the eyeball to be observed and arranged to observe through said holder from a position corresponding to the exit end of the selected optical fiber bundle.

5. A device for ophthalmoscopy according to claim 4, in which said holder comprises a tubular contact lens holder carrying said contact lens at one end thereof and a tubular optical fiber bundle holder carrying said optical fiber bundles arranged in substantially longitudinal direction of said optical fiber bundle holder, said optical fiber bundle holder being separably fitted to said contact lens holder.

6. A device for ophthalmoscopy according to claim 5 further comprising a handle mounted to said tubular optical fiber bundle holder, said optical fiber bundles being passed through the inside of said handle.

7. A device for ophthalmoscopy according to claim 6, in which said selector shutter is mounted to said handle.

8. A device for ophthalmoscopy according to claim 4, in which said exit ends of said optical fiber bundles are arranged in planes which do not include the optical axis of said contact lens but are inclined toward a pre-determined direction by a predetermined angle so that illuminating light from said exit ends does not intersect with the optical axis of said contact lens.

* * * * *